United States Patent [19]
Valenty

[11] Patent Number: 5,747,018
[45] Date of Patent: May 5, 1998

US005747018A

[54] NITROCELLULOSE-FREE AQUEOUS NAIL POLISH COMPOSITIONS

[75] Inventor: Vivian B. Valenty, Tempe, Ariz.

[73] Assignee: VB Cosmetics Inc., Chandler, Ariz.

[21] Appl. No.: 728,152

[22] Filed: Oct. 9, 1996

Related U.S. Application Data

[63] Continuation-in-part of Ser. No. 415,143, Mar. 29, 1995, abandoned, which is a continuation of Ser. No. 114,502, Aug. 31, 1993, abandoned.

[51] Int. Cl.$^6$ .................................................. A61K 7/043
[52] U.S. Cl. ........................................................... 424/61
[58] Field of Search ............................................... 424/61

[56] References Cited

U.S. PATENT DOCUMENTS

| | | | |
|---|---|---|---|
| 4,158,053 | 6/1979 | Greene et al. | 424/61 |
| 4,495,172 | 1/1985 | Orlowski et al. | 424/61 |
| 4,891,213 | 1/1990 | Gordon et al. | 424/61 |
| 4,897,261 | 1/1990 | Yamazaki et al. | 424/61 |
| 4,946,932 | 8/1990 | Jenkins . | |
| 5,102,654 | 4/1992 | Castrogiovani et al. | 424/61 |
| 5,120,529 | 6/1992 | Koch et al. | 424/61 |
| 5,266,322 | 11/1993 | Myers et al. | 424/61 |
| 5,380,520 | 1/1995 | Dobbs | 424/61 |
| 5,474,843 | 12/1995 | Lambert et al. | 428/337 |

OTHER PUBLICATIONS

"Fast Drying Aqueous Nail Polish," Research Disclosure, Jun. 1991, No. 32620, Disclosed Anonymously.

*Primary Examiner*—Robert H. Harrison
*Attorney, Agent, or Firm*—Antonio R. Durando; Harry M. Weiss

[57] ABSTRACT

Novel thickening agents for nitrocellulose-free, aqueous dispersions of sulfonate-containing polymeric resins have been found to materially improve the adhesive properties of these resins in nail polish formulations. One type of additives comprises fine organic and inorganic powders that are added to the resin suspension. Other types comprises neutral water-soluble polymers. When used in combination, the water-soluble polymers not only act as thickeners but also keep the fine powders in suspension, thus providing a more uniform colloidal mixture for application to nails.

14 Claims, No Drawings

NITROCELLULOSE-FREE AQUEOUS NAIL POLISH COMPOSITIONS

This application is a continuation-in-part of Ser. No. 08/415,143, filed on Mar. 29, 1995 now abandoned, which is a file-wrapper continuing application of abandoned Ser. No. 08/114,502, filed Aug. 31, 1993, all by the same inventor.

BACKGROUND OF THE INVENTION

1. Field of the Invention

This invention pertains to the general field of clear and pigmented base coats for lacquers and enamels applied to human nails. In particular, the invention relates to compositions that utilize a sulfonate group-based polymeric blend as primary film former.

2. Background of the Invention

Nail polishes (including clear base and top coats), lacquers and enamels comprise a class of products regularly used by modern women as part of their beauty care regimen. The process of applying enamels to nails requires that three to four different layers of coating be applied and allowed to dry. Typically, a first layer of colorless base coat is applied, then two layers of color enamel and, finally, a layer of colorless polish (top coat) for gloss and protection.

Nitrocellulose is normally used as the primary film-former resin in base-coat, colored nail-polish and top-coat formulations because it dries quickly, it has high gloss and it is abrasion resistant. Its disadvantages are that it is highly flammable and it turns from colorless to yellow upon exposure to sunlight. In addition, the solvents used in nitrocellulose formulations are also flammable. Therefore, a replacement for nitrocellulose as the primary film former has been a desirable development in the nail polish industry for some time.

U.S. Pat. No. 4,946,932 to Jenkins (1990) and Research Disclosure No. 32620 (1991) describe the use of aqueous dispersions of sulfonate group-containing polymers as nitrocellulose substitutes for nail polish formulations. These polymers are disclosed in combination with conventional additives to provide acceptable adhesion, gloss, drying time, water resistance, and other desirable nail polish properties. Aqueous dispersions of the type described in these disclosures are commercially available from the Eastman Kodak Company of Rochester, N.Y., under the trademark "Aquarez 7" for use in nail polish, including base and top coats.

The important feature of these compositions of mixtures of organic copolymers dispersed in water is that they dry as fast as solutions of nitrocellulose in organic solvents. Without limiting the scope of this disclosure, a theoretical explanation for this property may be that the sulfonate groups in the polymers react with the keratin's amide groups and/or with the aminoacids' amine groups in the nail of a user to form a chemical bond with the surface of the nail. This reaction liberates water molecules that would otherwise be solvated to the sulfonate groups and allows them to migrate to the surface of the coat and to evaporate rapidly. In addition, the bonds improve the adhesion of the polymeric coating to the nail.

In the course of evaluating "Aquarez 7" resins as base coats for a manicure, I found that the resulting manicure recedes from the edges after drying. Also, the dried film develops an undesirable tacky surface when used as a top coat. When used in conjunction with a commercial quick drying topcoat, the resulting manicure is glossy and non-tacky, but highly wrinkled and it still recedes from the edges. These characteristics result from the fact that the viscosity of these polymeric products in aqueous dispersion is too low for direct use in nail polishes; therefore, the products need to be thickened before use.

Experiments have shown that aqueous dispersions of sulfonate group-containing polymers cannot be thickened simply by increasing the polymer concentration in the mixture because the dispersed polymer particles will separate before the dispersion is sufficiently thickened for use in nail polish formulations. Therefore, the dispersions need to be thickened by means of additives.

Smectite clays, such as hectorite and bentonite, are the rheology modifiers commonly used by those skilled in the art to increase the viscosity of nail polishes. In spite of repeated attempts with several formulations typically employed in the art, I found that smectite clays alone do not work as viscosity enhancers of aqueous dispersions of sulfonate group-containing polymers, such as the "Aquarez" products.

For example, a 1.0 g of "Hectabrite DP" (a trademark for a smectite clay sold by the American Colloid Company of Arlington Heights, Ill.) added to 46 g of deionized water produces a gelatinous dispersion, showing that this clay will efficiently thicken dilute aqueous solutions, as expected. When 0.1 g of "Hectabrite DP," either as-is or pre-gelled in 0.5 g of deionized water, were added to 4.6 g of "Aquarez 7," no thickening occurred, contrary to expectation.

Similarly, water-soluble polymers, such as polyacrylic acids (carbomers), are common thickening agents that someone skilled in the art would use to increase the viscosity of an aqueous dispersion. Accordingly, 0.12 g of "Carbopol 974P," a carbomer product sold by the B. F. Goodrich Company of Brecksville, Ohio, were added to 48.5 g of water, heated and then neutralized, producing a gel, as expected. When 2.0 g of the gel so produced were added to 3.6 g of "Aquarez 7," though, thickening did not result, which was unexpected. The same result was obtained by adding the carbomer directly to the "Aquarez 7" suspension. This is believed to be due to the ionizable carboxyl groups contained in the carbomer molecule.

Therefore, there remains a need for new additives that can be used effectively to increase the viscosity of aqueous dispersions of sulfonate group-polymers without affecting the adhesive and quick-drying properties of these polymeric dispersions.

SUMMARY OF THE INVENTION

An object of the present invention is to provide a thickening additive for aqueous dispersions of sulfonate-containing polymers that is compatible for use in nail polishes.

In particular, an object of the invention is to provide additives that improve the adhesive and quick-drying properties of aqueous dispersions of sulfonate-containing polymers when applied on a nail, thus correcting the above-described problems of tackiness and recession.

A further object is to provide an adequately thickened composition that is compatible for use with commercially available nail polishes, lacquers and enamels.

Finally, a goal of the invention is to provide a product that does not irritate or sensitize the skin of a user.

Therefore, according to these and other objectives, the present invention consists of two classes of novel thickening agents for nitrocellulose-free, aqueous dispersions of sulfonate-containing polymeric resins that have been found to materially improve the adhesive properties of these resins in nail polish formulations. One type of additives comprises fine organic and inorganic powders that are added to the resin suspension. The other type comprises neutral water-soluble polymers. As used herein, a neutral or non-ionic water-soluble polymer is defined as a water-soluble polymer that is non-ionic and remains non-ionic when mixed with the water dispersion of a sulfonate-containing polymer. When used in combination, the water-soluble polymers not only act as thickeners but also keep the fine powders in suspension, thus providing a more uniform colloidal mixture for application to nails.

Various other purposes and advantages of the invention will become clear from its description in the specification and examples that follow and from the novel features particularly pointed out in the appended claims. However, such examples and description disclose only some of the various ways in which the invention may be practiced and should not be construed to limit its scope in any way.

DETAILED DESCRIPTION OF THE PREFERRED EMBODIMENT

The heart of this invention lies in finding suitable thickening agents for aqueous dispersions of sulfonate-containing polymeric resins in order to improve their adhesive properties and uniformity of application during manicures. By so improving the characteristics of these water-based resins, they become available as desirable substitutes for the organic-based nitrocellulose resins conventionally used in nail-polish products.

My first discovery is that the addition of fine, water-insoluble powders (both inorganic and organic) to aqueous dispersions of sulfonate-containing polymer resins produces a finished manicure that does not recede from the edges after drying. This was achieved simply by dispersing powders such as fumed silica and titanium dioxide, in particle sizes between 0.1 microns and 50 microns, in a water-based sulfonate-containing polymer or polymer blend. The viscosity and homogeneity of the resulting mixture was thus increased; yielding a better product for uniform application. I found that it produced a manicure that dried faster than the base polymer dispersion and exhibited none of the undesirable characteristics noted above. Adhesion to natural nails was also improved when compared to commercial nitrocellulose-based coats. Following are some examples of mixtures used.

EXAMPLE 1

| Ingredient | Weight Percent |
| --- | --- |
| "Aquarez 7" [A blend of copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 95.00 |
| Fumed silica | 5.00 |

The fumed silica used in Example 1 is a product sold by Degussa Corporation of Dublin, Ohio, under the trademark "OK412."

As illustrated in Example 2 below, other powders that might be used in place of or in combination with fumed silica are fine powders of titanium dioxide, which have the added advantage of serving as ultraviolet light screens. Since UV light is the cause of yellowing and discoloration in nail polishes, the use of titanium dioxide as a thickening agent provides this additional useful function.

EXAMPLE 2

| Ingredient | Weight Percent |
| --- | --- |
| "Aquarez 7" [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 99.00 |
| Titanium dioxide | 1.0 |

Other finely ground (having a particle size not to exceed 50 microns) water-soluble inorganic powders may be used, such as boron nitride, smectite clays, silica, zinc oxide, iron oxides, calcium and magnesium carbonates, and lakes. Because lakes are available commercially in various colors as FDA-approved products for nail polishes (such as the various aluminum, zirconium, barium, strontium, potassium and calcium lakes sold by chemical companies such as Universal Foods Corporation of Plainfield, N.J., and Seltzer Chemicals Inc. of Carlsbad, Calif.), they are particularly useful as thickening agents for colored nail polishes.

I found that finely ground, water-insoluble organic powders are also suitable thickening agents for sulfonate-containing polymers dispersed in water. These agents comprise microcrystalline cellulose, polyaromatic amides (sold by The DuPont Company under the trademark "Kevlar"), polyethylene, nylon, and polyester, used either alone or in combination with the finely ground inorganic material described above.

EXAMPLE 3

| Ingredient | Weight Percent |
| --- | --- |
| "Aquarez 7" [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 92.5 |
| Microcrystalline cellulose (50µ) | 7.5 |

I found that all of the disclosed water-insoluble powders are very effective as thickening agents at concentrations in the range from 0.1 to 10.0 percent by weight of the total composition. The preferred range is from 0.2 to 5.0 percent by weight for the inorganic powders and from 0.2 to 7.5 percent by weight for the organic powders. The powders are ground to a particle size not to exceed 50 microns and thoroughly mixed in the water dispersion of sulfonate-containing polymer, causing the powder to also become dispersed in the colloidal mixture, a procedure that would be obvious to those skilled in the art. The preferred particle size for these powders is from 0.1 to 25 microns.

In contrast to a base coat using the unmodified sulfonate-containing resin, a finished manicure produced by using this invention does not recede from the edges after drying. Moreover, when used in conjunction with commercial quick-drying top coats, the resin of this invention produces a manicure that is glossy, non-tacky and smooth.

My second discovery is that non-ionic (neutral) water-soluble polymers and copolymers that do not react chemically with the sulfonate-containing polymer are also effective thickeners for the sulfonate-containing polymeric dispersions of this invention. Especially in conjunction with the fine insoluble powders described above, improved aqueous formulations of the sulfonate-containing polymers are obtained. I found that these additives result in manicure formulations that produce a uniform coat over a person's nails by application with conventional nylon brushes that are most commonly used in the industry; this is difficult to achieve with the original thinner water suspension. The thicker coating provides ridge-filling of the nail surface, which produces a more uniform and smoother result. Contrary to what a skilled formulator might speculate, dilution of the sulfonate-containing polymer by the addition of the water-soluble polymer does not decrease the drying qualities of the dispersion and the hardness of the resultant film, nor the adhesion of the coating to the keratin of the nail. Rather, it improves the drying qualities of the polymeric dispersion and provides a harder dried coating than the original dispersion.

In water-dispersed sulfonate-containing polymers or polymer blends having a preferred concentration between 20 and 60 percent by weight of total composition, most preferably between 30 and 45 percent by weight, the neutral water-soluble polymers not only act as thickeners but also keep the fine powders suspended in the polymer solution, thus providing a more uniform product for application. Furthermore, the addition of these polymer water solutions to the coating formulation affords sufficient solubility to the fresh resin in the outside layers of the coating for easier clean-up of the brush and skin around the nail.

Depending on the specific sulfonate-containing polymer used, the composition sometimes tends to thicken over time, producing a deterioration in the quality of the product. I found that in those instances lowering the concentration of sulfonate-containing polymer below 20 weight percent of total composition, down to concentrations as low as 5 percent, produces a longer shelf life, which may be desirable even though the product may not be as attractive as with a higher concentration.

Any water-soluble polymer that is non-ionic and remains non-ionic after mixing with the sulfonate-containing polymer, in concentrations between 0.1 and 10.0 percent by weight of total composition, is believed to be suitable for practicing this invention. For instance, I found that polyvinyl alcohol, hydroxyethyl cellulose and polyoxyethylene provide excellent results. Without intending to limit the scope of the invention, other examples of suitable polymers comprise either synthetic or natural polyhydroxylic polymers such as polyvinyl alcohol, hydroxymethyl cellulose, hydroxyethyl cellulose, hydroxypropyl cellulose, hydroxypropyl methylcellulose, polyglycerol, polyglyceryl esters, starches (modified and unmodified), dextrans, ethers and esters thereof, and copolymers thereof; other water-soluble polymers such as polyoxyethylene, polyoxypropylene, polyvinyl pyrrolidone, and partially hydrolyzed polyvinyl acetates, and copolymers thereof; and mixtures of any of these compounds. The preferred concentration of non-ionic water-soluble polymers is between 0.5 and 5.0 percent by weight of total composition.

As would be obvious to one skilled in the art, the additive polymer solution is prepared by dispersing polymer particles in cold water and heating the mixture to a temperature sufficient to cause the dissolution of the polymer while stirring until complete dissolution is achieved. The solution is allowed to cool to room temperature and the fine-ground water-insoluble powder is added and mixed thoroughly to form a uniform dispersion. This dispersion is then added slowly to the aqueous sulfonate-containing dispersion. Alternatively, the water-insoluble powder may be dispersed first before the addition of the water-soluble polymer to the cold water dispersion; or the water-insoluble powder and water-soluble polymer may be dry mixed and then added at the same time to the cold water under vigorous agitation. Preservatives, such as paraben or equivalent compounds used in the art, may be added to prevent the growth of microorganisms in the aqueous formulation, thus prolonging the shelf life of the product and inhibiting its spoilage by microbial contamination during use.

The invention is further described in the following examples, which are not to be construed as limiting the scope of the appended claims. These are examples of non-pigmented formulations for a colorless basecoat:

EXAMPLE 4

| Ingredient | Weight Percent |
|---|---|
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 40.7) |
| Deionized Water | 40.0–65.0 (preferably 57.8) |
| Polyvinyl Alcohol | 0.1–10.0 (preferably 1.0) |
| Micronized $TiO_2$ (25µ) | 0.2–5.0 (preferably 0.5) |

The mixture of Example 4 was prepared as follows. Polyvinyl alcohol was dispersed in cold water and heated to 80° C. with stirring until complete dissolution was achieved. Upon cooling to room temperature, the titanium dioxide was added and mixed thoroughly. This dispersion was then added slowly to the Aquarez 7 product.

EXAMPLE 5

| Ingredient | Weight Percent |
|---|---|
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 34.9) |
| Deionized Water | 40.0–65.0 (preferably 63.5) |
| Polyvinyl alcohol | 0.1–10.0 (preferably 1.0) |
| Titanium dioxide (25µ) | 0.2–5.0 (preferably 0.5) |
| Parabens (esters of para-hydroxy benzoic acid) | 0.1–1.0 (preferably 0.1) |

EXAMPLE 6

| Ingredient | Weight Percent |
| --- | --- |
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 39.6) |
| Deionized Water | 40.0–65.0 (preferably 59.2) |
| Polyvinyl alcohol | 0.1–10.0 (preferably 1.0) |
| Hectorite (25μ) | 0.2–5.0 (preferably 0.2) |

EXAMPLE 7

| Ingredient | Weight Percent |
| --- | --- |
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 40.8) |
| Deionized Water | 40.0–65.0 (preferably 59.2) |
| Hydroxypropyl Methylcellulose | 0.1–10.0 (preferably 0.3) |
| Boron Nitride (25μ) | 0.2–5.0 (preferably 0.3) |

The novel combination of non-ionic water-soluble polymers and fine powders as additives to the aqueous dispersion of a sulfonate-containing polymer is especially important for achieving colored formulations of nail polishes. Finely ground iron oxides in combination with colored pigments and dyes (such as available from the Universal Foods Corporation of Plainfield, N.J., or the Sun Chemical Corporation of Staten Island, N.Y.) can be anticipated to work well in the mixtures of the invention to produce colored polishes. To this end, other additives have to be incorporated. For example, water-soluble dyes and finely ground FDA-approved lakes, in concentrations required to produce the desired coloration, would be suitable colorants. As is well understood by those skilled in the art, since a high loading of the finely ground powders is required for opacity and good color coverage, flow modifiers such as low molecular-weight hydroxylic compounds (for example glycerol, glycols, etc.), in concentrations between 1.0 and 25.0 percent by weight of total composition, and conventional defoamers such as silicone/polyhydroxy copolymers, acetylated triglycerides, polypropylene glycols, etc., in concentrations between 0.1 and 10.0 percent by weight of total composition, may be necessary. It is to be noted that conventional surf actants, such as fatty acid esters of polyoxyethylene or fluorinated surfactants, are not as effective and are less desirable as flow modifiers because they affect the surface tension of the product and cause undesirable foaming during processing and during application of the product. As mentioned above, preservatives may also be added to prolong the shelf life of the product. Conventional aqueous-formulation preservatives, such as parabens (para-hydroxy benzoic acid esters), hydroxyglycinate, and imidazolidinyl urea, in concentrations between 0.05 and 1.0 percent by weight of total composition, are suitable to practice the invention.

The following are examples of colored formulations of the present invention:

EXAMPLE 8

| Ingredient | Weight Percent |
| --- | --- |
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 31.3) |
| Deionized Water | 40.0–65.0 (preferably 43.9) |
| Polyvinyl alcohol | 0.1–10.0 (preferably 0.5) |
| Glycerol | 1.0–25.0 (preferably 16.1) |
| Polysiloxane defoamer (10% in water) | 0.1–10.0 (preferably 3.2) |
| Polyvinyl pyrrolidone | 0.0–5.0 (preferably 1.0) |
| Titanium Dioxide | 0.0–5.0 (preferably 1.2) |
| Hectorite (a smectite clay) | 0.0–5.0 (preferably 2.5) |
| D&C Red #44 and D&C Red #33 mixture | 0.0–5.0 (preferably 0.3) |

EXAMPLE 9

| Ingredient | Weight Percent |
| --- | --- |
| [copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer, the blend being emulsified with ammonium nonoxynol-4 sulfate] | 25.0–45.0 (preferably 34.9) |
| Deionized Water | 40.0–65.0 (preferably 63.5) |
| Polyvinyl alcohol | 0.1–10.0 (preferably 1.0) |
| Titanium dioxide (25μ) | 0.0–5.0 (preferably 0.4) |
| Boron Nitride (25μ) | 0.0–5.0 (preferably 0.1) |
| Parabens | 0.1–1.0 (preferably 0.1) |
| Beet powder (to desired coloration) | quantum sufficit |

Parabens, para-hydroxy benzoic acid esters, are available commercially from several manufacturers. For example, Uniphen P-23 is a trademark for a mixtures of methyl, ethyl, propyl, and butyl parahydroxybenzoate and phenoxyethanol sold by Induchem AG of Switzerland. Similarly, red beet powder is available commercially from Freeman Industries, Inc. of Tuckahoe, N.Y..

The colored nail polishes derived from the above compositions dry within 3 minutes after application, comparable with traditional solvent-based nitrocellulose products. To obtain a manicure with high gloss, the following method of application is recommended:

a. Cleaning the surface of the nail with an oil-free nail polish remover.

b. Applying a colorless aqueous nail polish formulation, such as one of the base coat formulations described above that contain no dye or pigment. A layer of a conventional (solvent-based) base coat may be applied on top of this aqueous base coat to prevent staining of the nail by subsequent layers of colored polish. This added step produces a surface that is compatible with all conventional colored nail polishes.

c. Applying at least one coat of a colored formulation based on the color nail polish formulations described above, drying the nail polish in air or by applying heat before a succeeding layer is applied.

d. Finally, applying a final top coat of a solvent-based colorless nail polish to seal the manicure, so as to prevent chipping, scratching and destruction by water.

As exemplified by this suggested preferred method of application, the nitrocellulose-free resin formulations of this invention are compatible for use in conjunction with solvent-based nail polishes.

As would be appreciated by one skilled in the art, the chemicals used in the preparation of these formulations were selected, in part, because they are non-toxic and generally non-photoallergenic.

While the invention has been particularly shown and described with reference to a preferred embodiment thereof, it will be understood by those skilled in the art that changes in form and detail may be made therein without departing from the spirit and the scope of the invention.

I claim:

1. An aqueous nail polish composition, comprising:
 a water dispersion of a sulfonate-containing polymer, copolymer or polymer blend;
 a water-soluble polymer or copolymer dissolved in water and mixed with said water dispersion of a sulfonate-containing polymer, copolymer or polymer blend, said water-soluble polymer or copolymer being non-ionic when mixed with said water dispersion of a sulfonate-containing polymer, copolymer or polymer blend; and
 a water-insoluble finely-ground powder material suspended in said water dispersion;
 said powder material having a particle size not to exceed 50 microns and being present in a concentration between 0.1 and 10.0 percent by weight of total composition; said water-soluble non-ionic polymer or copolymer being present in a concentration between 0.1 and 10.0 percent by weight of total composition; and said sulfonate-containing polymer, copolymer or polymer blend being present in a concentration between 5 and 60 percent by weight of total composition.

2. The composition of claim 1, wherein said powder material is selected from the group consisting of fumed silica, titanium dioxide, boron nitride, smectite clays, silica, zinc oxide, iron oxides, calcium carbonates, magnesium carbonates, lakes, microcrystalline cellulose, polyaromatic amides, polyethylene, nylon, polyester, and mixtures thereof.

3. The composition of claim 2, wherein said powder material is present in a concentration from 0.2 to 5.0 percent by weight of total composition and has a particle size between 0.1 and 25 microns.

4. The composition of claim 1, wherein said powder material is selected from the group consisting of fumed silica, titanium dioxide, boron nitride, smectite clays, silica, zinc oxide, iron oxides, calcium carbonates, magnesium carbonates, lakes, and mixtures thereof.

5. The composition of claim 1, wherein said powder material is selected from the group consisting of microcrystalline cellulose, polyaromatic amides, polyethylene, nylon, polyester, and mixtures thereof.

6. The composition of claim 1, wherein said water-soluble non-ionic polymer or copolymer is selected from the group consisting of synthetic polyhydroxylic polymers, natural polyhydroxylic polymers, copolymers thereof, and mixtures thereof.

7. The composition of claim 1, wherein said water-soluble non-ionic polymer or copolymer is selected from the group consisting of polyvinyl alcohol, hydroxymethyl cellulose, hydroxyethyl cellulose, hydroxypropyl cellulose, hydroxypropyl methylcellulose, polyglycerol, polyglyceryl esters, starches, dextrans, ethers and esters thereof, polyoxyethylene, polyoxypropylene, polyvinyl pyrrolidone, partially hydrolyzed polyvinyl acetates, and copolymers or mixtures thereof.

8. The composition of claim 6, wherein said water-soluble non-ionic polymer or copolymer is present in a concentration between 0.5 and 5.0 percent by weight of total composition; and said sulfonate-containing polymer, copolymer or polymer blend is present in a concentration between 30 and 45 percent by weight of total composition.

9. The composition of claim 8, wherein said powder material has a particle size not to exceed 25 microns and is present in a concentration between 0.2 and 5.0 percent by weight of total composition.

10. An aqueous nail polish composition, comprising:
 a water dispersion of a sulfonate-containing polymer, copolymer or polymer blend; and
 a water-soluble polymer or copolymer dissolved in water and mixed with said water dispersion of a sulfonate-containing polymer, copolymer or polymer blend, said water-soluble polymer or copolymer being non-ionic when mixed with said water dispersion of a sulfonate-containing polymer, copolymer or polymer blend;
 wherein said water-soluble non-ionic polymer or copolymer is present in a concentration between 0.1 and 10.0 percent by weight of total composition; and said sulfonate-containing polymer, copolymer or polymer blend is present in a concentration between 5 and 60 percent by weight of total composition.

11. The composition of claim 10, wherein said water-soluble non-ionic polymer or copolymer is selected from the group consisting of synthetic polyhydroxylic polymers, natural polyhydroxylic polymers, copolymers thereof, and mixtures thereof.

12. The composition of claim 10, wherein said water-soluble non-ionic polymer or copolymer is selected from the group consisting of polyvinyl alcohol, hydroxymethyl cellulose, hydroxyethyl cellulose, hydroxypropyl cellulose, hydroxypropyl methylcellulose, polyglycerol, polyglyceryl esters, starches, dextrans, ethers and esters thereof, polyoxyethylene, polyoxypropylene, polyvinyl pyrrolidone, partially hydrolyzed polyvinyl acetates, and copolymers or mixtures thereof.

13. The composition of claim 10, wherein said water-soluble non-ionic polymer or copolymer is present in a concentration between 0.5 and 5.0 percent by weight of total composition; and said sulfonate-containing polymer, copolymer or polymer blend is present in a concentration between 30 and 45 percent by weight of total composition.

14. An aqueous nail polish composition, comprising the following ingredients in the specified concentration ranges:

| Ingredient | Weight Percent |
|---|---|
| A blend of copoly(vinyl acetate/dibutyl maleate), terpoly (acetoacetoxyethyl methacrylate/ butyl acrylate/ethyl methacrylate), and diglycol/cyclohexanedimethanol/isophthalates/ sulfoisophthalates copolymer | 25.0–45.0 |
| deionized Water | 40.0–65.0 |

-continued

| Ingredient | Weight Percent |
|---|---|
| polyvinyl alcohol | 0.1–10.0 |
| titanium dioxide | 0.2–5.0 |
| parabens | 0.1–1.0 |

\* \* \* \* \*